(12) United States Patent
Bermudes (10) Patent No.: US 8,956,859 B1
(45) Date of Patent: Feb. 17, 2015

(54) COMPOSITIONS AND METHODS FOR DETERMINING SUCCESSFUL IMMUNIZATION BY ONE OR MORE VACCINES

(75) Inventor: David G. Bermudes, Woodland Hills, CA (US)

(73) Assignee: Aviex Technologies LLC, New Haven, CT (US)

( * ) Notice: Subject to any disclaimer, the term of this patent is extended or adjusted under 35 U.S.C. 154(b) by 714 days.

(21) Appl. No.: 13/209,573

(22) Filed: Aug. 15, 2011

Related U.S. Application Data (60) Provisional application No. 61/373,375, filed on Aug. 13, 2010.

(51) Int. Cl.
*C12M 1/34* (2006.01)
*G01N 33/558* (2006.01)

(52) U.S. Cl.
CPC .......... *G01N 33/558* (2013.01); *Y10S 435/805* (2013.01); *Y10S 435/97* (2013.01)
USPC ........ 435/287.7; 422/420; 422/425; 435/805; 435/970; 436/513; 436/514; 436/525

(58) Field of Classification Search
None
See application file for complete search history.

(56) References Cited

U.S. PATENT DOCUMENTS

| 4,943,522 | A | * | 7/1990 | Eisinger et al. | 435/7.25 |
| 5,354,692 | A | * | 10/1994 | Yang et al. | 436/514 |
| 5,384,264 | A | * | 1/1995 | Chen et al. | 436/525 |
| 5,559,041 | A | * | 9/1996 | Kang et al. | 436/518 |
| 5,602,040 | A | * | 2/1997 | May et al. | 436/514 |

* cited by examiner

*Primary Examiner* — Chris L Chin
(74) *Attorney, Agent, or Firm* — Steven M. Hoffberg; Ostrolenk Faber LLP (57) ABSTRACT

A host antigen-specific antibody testing system and method. The a ternary complex of the antigen, a ligand-bound anti-host IgM, and a non-host anti-antigen IgG detector conjugate selectively form a quaternary complex with host antibodies, wherein the host antibodies and IgG compete for the antigen, and the IgM binds the host antibodies. The quaternary complex is retained by an immobilized IgM ligand binding agent, and any residual ternary is retained by a later encountered immobilized anti-non-host IgG. If sufficient host antibodies have a high affinity for the antigen, the complex is detected at the quaternary complex detection region based on the presence of the detector, and if there are insufficient high affinity host antibodies, the ternary complex migrates past the quaternary complex detection region and is retained and detected at a control region.

20 Claims, 4 Drawing Sheets

EKEGSYPKLKNSggg DYKDDDDK gggAGPR↓SLX ggg HHHHHH

[SEQ ID NO: 008]

Fig. 3B

EKKGSYPKLKNSggg DYKDDDDK gggAGPR↓SLX ggg HHHHHH

[SEQ ID NO: 009]

Fig. 3C

| Test | Patient 1 | Patient 2 | Patient 3 |
|---|---|---|---|
| | Positive/ Positive E1/ E2 | Positive/ Negative E1/ E2 | Negative/ Positive E1/ E2 |
| Strip Assay Test |  |  |  |
| Control Band | + + | + + | + + |
| Test Band | + + | + - | - + |

Fig. 4

Only positive control tests shown

COMPOSITIONS AND METHODS FOR DETERMINING SUCCESSFUL IMMUNIZATION BY ONE OR MORE VACCINES

CROSS REFERENCE TO RELATED APPLICATIONS

This application is a non-provisional of, and claims benefit of priority from, U.S. Provisional Patent Application Ser. No. 61/373,375, filed Aug. 13, 2010, the entirety of which is expressly incorporated herein by reference.

1. FIELD OF THE INVENTION

This invention is related to the field of diagnostic methods and kits relating to immune responses of a host, including humans.

2. BACKGROUND OF THE INVENTION

Citation or identification of any reference herein, or any section of this application shall not be construed as an admission that such reference is available as prior art to the present application. The disclosures of each of these publications are hereby incorporated by reference in their entirety in this application, and shall be treated as if the entirety thereof forms a part of this application.

In the United States, conventional influenza types A or B viral epidemics can cause illness in 10% to 20% of people and are associated with an average of 36,000 deaths and an estimated 120,000-200,000 hospitalizations per year (estimates vary to do complications of pneumonia). In the advent of a highly pathogenic avian type influenza pandemic, the potential for severe morbidity and mortality will be substantially higher, and will occur during a time where the healthcare system is overburden. Many people will receive prior vaccination. During conventional epidemics, those receiving a vaccine do so with the presumption that 1) the vaccination will be successful and 2) that the vaccine matches the emerging pathogenic strain. Prior to, and during, a pandemic of highly pathogenic avian influenza or other influenza strain, those two assumptions may be inaccurate, yet, at the present time, there is no readily available means for people to determine if these immunization criteria have been met.

Currently established serological methods for detection of antibodies to influenza are necessary to conduct clinical trials of influenza vaccination, but are technical in nature, not accessible to the general public, and do not compare results for different antigens that would allow determination of which vaccine may have been successful when one or more vaccines has been administered (Cheng et al., 2008, Serologic and genetic characterization analysis of a highly pathogenic influenza virus (H5N1) isolated from an infected man in Shenzhen, J. Med. Virol. 80: 1058-1064; Katz et al., 1999, Antibody response in individuals infected with avian influenza A (H5N1) virus and detection of anti-H5 antibody among household and social contacts. J. Infect. Dis. 180: 1763-1770; Rowe et al., 1999, detection of antibody to avian influenza A (H5N1) virus in human serum using a combination of serologic assays, J. Clin. Microbiol. 37: 937-943).

Such methods determine the immune response, or seroconversion, in the host, which are specific antibody responses to vaccination or post viral infection, and should not be confused with diagnostics that determine the presence of the physical virus particle during infection such as described by Zambon and Ellis, 2001 (Molecular methods for diagnosis of influenza International Congress Series 1219: 267-273).

Following influenza vaccination performed in mid-1997 a study was performed by de Jong et al., (2001, Antibody responses in elderly to influenza vaccination in case of an antigenic mismatch, International Congress Series 1219: 707-711) wherein sera were obtained from vaccinees of various ages, including residents of nursing homes over 60 years of age. As a surrogate marker for induction of protection by influenza vaccination, they studied the haemagglutination inhibition (HI) antibody response of the vaccinees to vaccine and epidemic strains of the three (sub)types A(H3N2), A(H1N1), and B. Statistical methods included the paired t-test, the McNemar c2-test, the one-way ANOVA, the Pearson c2-test, and a "minimum-maximum" analysis, newly developed by Dr G. Lüchters from Bonn. In accordance with usual practice, the "50% protective threshold" of HI antibodies was set at 1:40 (Periera et al., 1972, Prevalence of antibody to current influenza viruses and effect of vaccination on antibody response. British Medical Journal 4:701-703).

In the influenza season of 1997/1998, a major antigenic mismatch of the H3N2 vaccine component occurred. They found that the vigor of immune responses declined at higher ages. Sera from influenza vaccinees was further used to assess the magnitude of this effect in case of an antigenic mismatch. At advanced age, the homologous antibody response was lowered, starting above 60 years. In addition, they found that the cross-reactivity of the formed antibodies to the drifted field virus decreased with age, starting above 70 years. They concluded that effect of ageing on the induction of "protective" titres (≥40) of HI antibodies against an emerging deviant strain can be severe, and that in the 1997/1998 season, in those above 80 years of age, the percentage of vaccinees acquiring such titres against the major epidemic H3N2 virus was only about 15%.

In the study by Keren et al., 2005 (Failure of influenza vaccination in the aged, J. Med. Virol. 25: 85-89), they found that in a cohort of 127 nursing home residents aged 60-98 years vaccinated during the winter of 1985-86 with the A-Chile 1/83 (c), A-Philippines 2/82 (p), and B-USSR (B) commercial influenza vaccines, that before vaccination 40%, 23%, and 69% were susceptible to influenza Ac, Ap, and B, respectively [hemagglutinin inhibition (H.I.) titer <1:40] and that one month following initial vaccination, 32 patients [25%] remained unprotected against two or all three vaccine strains. The unprotected patients were revaccinated with the same influenza vaccine and followed up. At five months 11%, 19%, and 23% of the initial cohort were still unprotected against Ac, Ap, and B strains, respectively. They conclude that two conventional influenza vaccines administered one month apart leave unprotected 30% of healthy elderly people who are initial influenza vaccine failures.

Physicians have long believed that the elderly often fail to generate a sufficient immune response for protection when given a standard seasonal flu shot, as illustrated in the studies by de Jong et al., 2001 and Keren et al., 2005 described above. About 90 percent of the estimated 36,000 people who die from flu-related causes in the United States each year are 65 and older, and account for an estimated 120,000 hospitalizations. Although fewer children die from influenza, infection results in an additional 20,000 hospitalizations per year, with a total up to 200,000 resulting from all influenza infections. Unfortunately, of those who are vaccinated with conventional vaccines, there is no convention regarding determination of the extent to which the vaccination was successful. The fact that the vaccine may not be antigenically matched to the emergent seasonal vaccine further compromises the overall protective effect on the population. Despite the obvious "leap-of-faith" in being vaccinated without determining effectiveness, there has been no apparent movement toward developing a diagnostic test that would inform a patient whether they were adequately protected.

Highly pathogenic H5N1 avian influenza presents a number of similar complications as conventional influenza as well as new challenges in effectively protecting individuals within a population. First, the vaccines for H5N1 have not been subjected to an epidemiological challenge for effectiveness (i.e., an actual pandemic); surrogate markers such as the level of anti-influenza antibodies are used to gauge effectiveness. It is generally accepted that an antibody level of 1:40 (higher numbers indicate better protection) is required to give 50% protection for a standard influenza. A number of vaccine makers have increased production of conventional-type vaccine for H5N1, and a number of biotechnology companies have introduced new approaches to generating novel vaccines and have shown the ability to generate anti-H5N1 antibodies, including the use of virus-like particles (Pusko et al., 2010, Recombinant H1N1 virus-like particle vaccine elicits protective immunity in ferrets against the 2009 pandemic H1N1 influenza virus, *Vaccine*, 28:4771-4776) or influenza proteins produced in tobacco plants (Lico et al., 2009, Plant-produced potato virus X chimeric particles displaying an influenza virus-derived peptide activate specific CD8+ T cells in mice. *Vaccine*, 27:5069-76). However, given the highly pathogenic nature of the H5N1 avian influenza (50-80% mortality), an antibody level of 40 may not be effective at all, at least on its own. Thus, a remarkably novel situation exists in terms of the number of different vaccine manufacturers and types of vaccines that may be available for H5N1 for which the ramifications have not been explored. This situation will also be complicated by differences in the antigens used to prepare the vaccine and their match to the emerging pathogen or pathogens. In countries where multiple types of vaccines are available, it seems probable that people will question the efficacy of individual vaccine types, which would require diagnostic testing in order to determine; a situation that has not been previously recognized and for which no solution has been proposed. The potential ineffectiveness of a single vaccine may lead many to seek a second vaccination using the same or an alternative vaccine type. While it would seem desirable to proceed to multiple vaccinations without testing, only through testing will the individuals within the population know if and/or when a vaccine or set of vaccines has been effective for them personally and will the medical field know which vaccines and/or combination of vaccines are effective within a population. The consequence of an unsuccessful vaccination and infection by H5N1 may be death, dramatically skewing the cost-benefit ratio analysis. Furthermore, in the advent of a shortage, the availability of a second vaccine for those already receiving an initial injection may not be justifiable without a diagnostic test indicating its necessity, even if the test were more expensive than the vaccine itself.

3. SUMMARY OF THE INVENTION

The present invention uses novel methods and provides a diagnostic kit for determining successful vaccination for influenza and other infectious diseases. Unlike conventional diagnosis of successful vaccination, the present invention provides simultaneous testing against multiple antigens containing "fingerprint" signatures that allows not only the determination of successful vaccination, but the ability to determine which vaccine was successful in the event multiple vaccines are administered to the same host. The diagnostic influenza vaccination test also provides information as to the strain(s) of influenza for which vaccination has been successful, as well as subtypes, immune escape variants, and neurominadase resistant strains. The diagnostic device and/or kit are particularly useful for highly pathogenic influenza, such as the H1N1 "swine" and H5N1 "avian" flu strains.

OBJECTS OF THE INVENTION

Influenza and vaccines for the prevention of influenza and the associated immune responses are used as a non-limiting illustrative example. The present invention comprises an in vitro diagnostic test that can be informative of the following:

1) Presence and semi-quantitative concentration of anti-influenza antibodies (i.e., successful immunization) to different influenza antigens.

2) Strain of influenza to which the antibodies belong, including conventional H1N1 and highly pathogenic H5N1 viruses and emergent subtypes. The complete set of subtypes for influenza A could include the 16 different hemagglutinin subtypes H1, H2, H3, H4, H6, H7, H8, H9 H10 H11, H12, H13, H14, H15 or H16 or 9 different neuraminidase subtypes N1 N2 N3 N4 N5 N6 N7 N8 or N9. The diagnostic proteins may also include one or more nucleoprotein (NP), M1, M2, NS1, NS2 (NEP), PA, PB1, PB1-F2 and/or PB2 which may or may not be present in certain vaccine preparations.

3) Type of vaccine that generated the immune response (where applicable in patients receiving more than one type of vaccine). The information may include specific characteristics including immune escape variants, or oseltamivir-resistant mutants (e.g., the H274Y mutation in the neuromimidase or other compensatory mutations; Bloom et al., Permissive secondary mutations enable the evolution of influenza oseltamivir resistance, Science 328: 1272-1275).

4) Under some circumstances, such as when one or more vaccine preparations do not have the entire protein content of the virus, such as being limited to the hemagglutinin and/or neurominadase, the test can determine the difference between infection by the wild-type virus or vaccination by one or more vaccines.

It is therefore an object to provide a system and method for testing for presence of an antibodies to an antigen from a host, comprising providing: a reactant layer, into which are absorbed the antigen, an anti-host immunoglobulin IgM antibody bound to a ligand, and a detector comprising a non-host anti-antigen IgG antibody conjugated to colloidal particles; a test strip, in fluid communication with the reactant layer at a portion thereof, to which is immobilized a ligand binding agent at a test area and anti-non-host IgG immobilized at a control area, the test area being spaced more proximate to the reactant layer than the control area; and a sample well.

A serum specimen from a host is placed in the sample well, and host antigen-specific antibodies in the specimen are permitted to selectively form a quaternary complex with the detector/antigen/IgM complex. The quaternary complex migrates through the test strip and is captured at the test area by the immobilized ligand binding agent. Detector/antigen/IgM complex unbound to antigen-specific host antibodies migrate through the test strip, past the test area, and are captured at the control area by the immobilized anti-IgG. A presence of the host antigen-specific antibodies is detected by an indication at the test area and validity of the test is ensured by an indication at the control area. The colloidal particles are preferably readily detectable, though other types of detectors may also be used in substitution for the colloidal particles.

It is a further object to provide a testing system and method for presence of an antibodies to a particular antigen from a host, comprising: providing a reactant layer, having a the particular antigen, an anti-host immunoglobulin IgM antibody bound to a ligand, and a non-host anti-antigen IgG antibody conjugated to a detector; forming a complex by adding serum containing host antibodies to the particular antigen, wherein the host antibodies and the IgG bind the particular antigen, and the IgM binds the host antibodies; migrating the complex on a strip toward a first region having an immobilized ligand binding agent which binds and ceases migration of the IgM antibody and any complexes including the IgM antibody; migrating residual of the complex past the first region to a second region having immobilized anti-non-host IgG immobilized at a control area, which binds the non-host IgG antibody and any complexes including the non-host IgG antibody, wherein, if the host antibodies have a high affinity for the antigen and are present in sufficient quantity, a complex comprising the antigen, the host antibodies, and the anti-host IgM antibodies and the non-host anti-antigen IgG and detector are retained in the first region for detection based on the presence of the detector, and if the host antibodies have a low affinity for the antigen or are not present in sufficient quantity, a complex comprising the antigen, the non-host anti-antigen IgG and detector, will migrate past the first region and b retained at the second region for detection based on the presence of the detector.

The ligand is preferably biotin and the ligand binding agent is preferably strepavidin.

The colloidal particles are preferably gold particles.

The concentrations of antigen, anti-host immunoglobulin IgM antibody bound to the ligand, the detector, immobilized ligand binding agent and immobilized anti-IgG are provided, based on calibration with pooled sera from successfully immunized hosts, to produce a positive indication at an IgM Index value of at least 1.1 of an IgM Capture ELISA device and a negative indication results below an IgM Index value of 1.1.

The antigen is, for example, an influenza hemaggutinin (e.g., hemagglutinin or neuraminidase), which may be produced by a bacterium. The antigen may comprise a gene product of an inserted gene in a genetically engineered bacterium. The antigen may be an influenza hemagglutinin produced by a genetically engineered bacterium, a non-glycosylated protein produced by a bacteria corresponding to a glycosylated protein produced by a virus during mammalian infection, produced in insect cells, a glycosylated antigen produced in an insect cell/baculovirus method, produced in an insect cell and has (or is absent) a hexahistidine tag, correspond to an influenza hemagglutinin antigen if an influenza strain which causes human disease, correspond to an influenza neuraminidase antigen of an influenza strain which causes human disease, an epitope peptide of a pathogenic influenza, and/or the epitope peptide may comprise an epitope hemagglutinin peptide modified to be covalently bound to a non-hemaggutinin epitope peptide.

The anti-host immunoglobulin IgM antibody bound to a ligand may comprise biotinylated goat-antihuman IgM.

The non-host anti-antigen IgG antibody may comprise mouse monoclonal IgG anti-antigen antibody.

The anti-IgG immobilized at the control area may comprise rabbit antimouse IgG-Fc. The mouse monoclonal IgG anti-antigen antibody may be conjugated onto colloidal gold particles.

The antigen, the anti-host immunoglobulin IgM antibody bound to a ligand, and the detector may be dispensed as at least one solution on the reactant layer and subsequently lyophilized.

The reactant layer may comprise a polyester pad. The test strip may comprise a nitrocellulose membrane. The test strip may comprise an elongated strip, on which the reactant layer is situated on one side, and the test area and control area are sequentially disposed distant from the test strip. The sample well may be provided on top of the reactant layer, and between the reactant layer and the test strip is disposed at least one flow control layer. The test system may further comprise an absorbent pad in fluid communication with the test strip disposed on an opposite side of the control area from the reactant layer, wherein the absorbent pad induces a bulk fluid flow from the reactant layer to the absorbent pad.

The method may further comprise vaccinating the host with the antigen, and/or vaccinating the host with multiple antigens concurrently.

The test may further comprise a plurality of control areas, each associated with response indicative of absence of antibodies to a different antigen, wherein for each different antigen, a corresponding anti-non-host IgG antibody having respectively different conserved portions, conjugated to colloidal particles is provided, and at each respective control area, a corresponding anti-non-host IgG specific for the respectively different conserved portions is immobilized.

4. BRIEF DESCRIPTION OF THE DRAWINGS

FIG. 1A shows an arrangement of different components in a strip test design and examples of positive (both bands present), negative (test band absent), and invalid (no control band) test results.

FIG. 1B shows tabular results of the test strip, in which positive test results are suggestive of influenza immunity as the IgM levels are at or above the established cut-off level, and invalid results indicate that the test must be repeated. rFLU, recombinant influenza antigen; Mab, monoclonal antibody.

FIGS. 2A and 2B shows a determination of an epitope region of a sequence based on known epitopic regions.

FIGS. 3A, 3B and 3C show a modification of an epitope for use in a strip assay determining the response to one or more epitopes.

FIG. 4 shows the tabular results of a test strip with two representative set of finger print peptide sequences for two epitopes (E1 and E2) of H1 hemagglutinins, where the first epitope is described in FIG. 3B and the second epitope is described in FIG. 3C.

5. DETAILED DESCRIPTION OF THE INVENTION

The present invention provides, according to various embodiments, compositions and methods for diagnosis of successful vaccination that can determine infectious subtypes for which an individual is vaccinated, and provides a means to distinguish between immune responses in vaccinees that have received more than one type of vaccine. The types of infectious diseases may generally include prions, viruses, bacteria, protozoans (protists), fungi and helminthes (Mandell, Bennett and Dolin 2010, Principles and Practices of Infectious Diseases, $7^{th}$ Edition, Elsiever Publishers, 4320 pages). A particularly useful application is for assessment of influenza vaccination.

For reasons of clarity, the detailed description is divided into the following subsections: 1) infectious types and subtypes, 2) antigens, 3) epitopes, 4) posttranslational modifications of antigens and epitopes, and 5) antibody-based tests.

5.1. Infectious Types and Subtypes.

There are three types of influenza viruses Influenza A, B, and C. Influenza type A viruses are divided into subtypes based on two proteins on the surface of the virus. These proteins are termed hemagglutinin (H) and neuraminidase (N). Influenza A viruses are divided into subtypes based on these two proteins. There are 16 different hemagglutinin subtypes H1, H2, H3, H4, H6, H7, H8, H9 H10 H11 H12, H13, H14, H15 or H16 and 9 different neuraminidase subtypes N1 N2 N3 N4 N5 N6 N7 N8 or N9, all of which have been found among influenza A viruses in wild birds. Wild birds are the primary natural reservoir for all subtypes of influenza A viruses and are thought to be the source of influenza A viruses in all other animals, such as pigs, giving rise to "swine flu" strains. The current subtypes of influenza A viruses found in people are A(H1N1) and A(H3N2). Influenza B virus is not divided into subtypes. Influenza A genome contains 11 genes on eight pieces of RNA, encoding for 11 proteins; hemagglutinin, neuraminidase (NA), nucleoprotein (NP), M1, M2, NS1, NS2 (NEP), PA, PB1, PB1-F2 and PB2 (Ghedin et al., 2005, Large-scale sequencing of human influenza reveals the dynamic nature of viral genome evolution. *Nature* 437: 1162-1166).

5.2. Antigens.

The antigens are those from the infectious disease for which one or more vaccines has been prepared, having identifiable sequences that may contain specific signature sequences. The signature sequences may comprise one or more amino acid sequence variations within an antigenic portion of the antigen, including subtype differences, immune escape forms, or drug resistant forms. The differences may include posttranslational modifications of the antigen. In the case of influenza A, the antigens are H1, H2, H3, H4, H6, H7, H8, H9 H10 H11 H12, H13, H14, H15 or H16 and 9 different neuraminidase subtypes N1 N2 N3 N4 N5 N6 N7 N8 or N9, as well as the nucleoprotein (NP), M1, M2, NS1, NS2 (NEP), PA, PB1, PB1-F2 and PB2.

5.3. Epitopes.

Epitope mapping, the determination of epitopes, uses processes known to those skilled in the arts and may include any methods known such as protease digestion/mass spectroscopy, spot membrane, phage peptide panning, monoclonal antibodies, hydrogen/deuterium exchange and/or crystallography in order to determine distinctive signature or fingerprint antigens (Morris (ed) Epitope Mapping Protocols, Humana Press, 1996; Joys and Schodel 1991. Infect. Immune. 59: 3330-3332; Hioe et al., 1990 J. Virol. 64: 6246-6251; Kaverin et al. 2002, J. Gen. Virol. 83: 2497-2505; Hulse et al. 2004, J. Virol. 78: 9954-9964; Kaverin et al. 2007, J. Virol. 81:12911-12917; Garcia et al., 2004, Hydrogen/deuterium exchange mass spectrometry for investigating protein-ligand interactions, ASSAY and Drug Development Technologies 2: 81-91; Kaverin et al., 2007, Epitope mapping of the hemaggluninin molecule of a highly pathogenic H5N1 influenza virus by using monoclonal antibodies, J. Virol. 81: 12911-12917; Hoffman et al., 2005, Role of specific hemagglutinin amino acids in the immunogenicity and protection of H5N1 influenza virus vaccines, PNAS 102: 12915-12920). T-cell epitope determination (Walden, 1996, Current Opinion in Immunology 8: 68-74) and computer programs such as Predict7 (Carmenes et al. 1989 Biochem. Biophys. Res. Comm 159: 687-693) and Pepitope (Mayrose et al., 2007. Bioinformatics 23: 3244-3246) or PepScan (Carter 1994, Epitope mapping of a protein using the Geysen (PEPSCAN) procedure. *Methods Mol. Biol.* 1994; 36:207-23; Philpott et al., 1989, Neutralizing epitopes of the H5 hemagglutinin from a virulent avian influenza virus and their relationship to pathogenicity, J. Virol. 63: 3453-3458). Similar forms or homologous eiptopes can be determined as described by Deem and Pan, 2009 (The epitope regions of H1-subtype influenza A with application to vaccine efficacy, Protein Engineering and Selection 22: 543-546) by aligning sequences using amino acid sequence alignment algorithms such as ClustalW or by alignment of three-dimensional structure using "homology modeling" (Nayeem et al., 2006, A comparative study of available software for high-accuracy homology modeling: From sequence alignments to structural models, Protein Sci 15: 808-824).

A fingerprint or signature antigen, and/or epitope within the antigen, is one that is present in one form of a vaccine, and different by at least one or more amino acids, or absent in another form, and such, that antibodies produced recognize the difference. A fingerprint or signature antigen, and/or epitope within the antigen, may include their posttranslational modifications which may be present in one form and altered or absent in another also such that antibodies recognize the difference.

Variations and immune escape examples have been published by several authors (Caton et al., 1982, The antigenic structure of the influenza virus A/PR/8/34 hemagglutinin (H1 subtype, Cell 982:417-27; Ferguson et al., 2003, Ecological and immunological determinants of influenza evolution, Nature 422: 428-433; Drescher et al., 1993, Comparative investigation of the hemagglutinin epitopes of influenza virus A/Brazil/11/78 (H1N1). and its escape variants, J Virol Methods, 42:75-88; Hensley et al., 2009, Hemagglutinin receptor binding avidity drives influenza A virus antigenic drift. Science 326: 734-736; Table 1), and new variants can be rapidly determined by comparing previous years amino acids sequences, such as within the hemagglutinin, with new sequences, within the well-known and defined epitope regions. The highly neutralizing epitopes of influenza hemagglutinin are designated Sa, Sb, Ca and Cb (Caton et al., 1982, The antigenic structure of the influenza virus A/PR/8/34 hemagglutinin (H1 subtype, Cell 982:417-27), where the "S" refers to strain specific antigenic determinants, and the "C" refers to constant antigenic determinants.

TABLE 1

EXAMPLES OF INFLUENZA HEMAGGLUTININ EPITOPE OR ANTIGENIC ESCAPE MUTANTS

| ANTIGEN | MUTATION | Epitope | REFERENCE |
| --- | --- | --- | --- |
| Hemagglutinin A/Puerto Rico/8/1934 H1N1 Hemagglutinin A/Vietnam/ | aa 158 E to K aa 246 E to G aa 156 E to K | Sa/Sb N/A Sb | Hensley et al., 2009, Hemagglutinin receptor binding avidity drives influenza A virus antigenic drift, Science 326: 734-728. EKEGSYPKLKNS [SEQ ID NO: 001] Kaverin et al., Epitope mapping of the hemagglutinin molecule of a highly pathogenic |

TABLE 1-continued

EXAMPLES OF INFLUENZA HEMAGGLUTININ EPITOPE OR ANTIGENIC ESCAPE MUTANTS

| ANTIGEN | MUTATION | Epitope | REFERENCE |
|---|---|---|---|
| 1203/04 H5N1 | | | H5N1 influenza virus using monoclonal antibodies. J Virol 81: 12911-12917 |

5.4. Posttranslational Modifications for Antigens and Epitopes

Viral proteins may include posttranslational modifications whereby structural and/or functional non-peptidal biosynthetic covalent modifications of the polypeptide are formed. Posttranslational modifications may include additions of phosphates, acetate, amines, lipids, sialic acid and carbohydrates. Carbohydrate structures, such as Gal alpha 1-3 Gal beta 1-4GlcNAc-R (termed the alpha-gal epitope) on viral glycoproteins is of interest because of the large amounts of natural antibody (anti-Gal) produced in humans against this epitope (Henion et al., 1997, Synthesis of alpha-gal epitopes on influenza virus vaccines, by recombinant alpha 1,3 galactosyltransferase, enables the formation of immune complexes with the natural anti-Gal antibody. *Vaccine* 15:1174-82). Because not all vaccines may contain glycosylated antigens, glycosylation of an antigen and/or a particular epitope may constitute a signature or fingerprint signature that can be used to distinguish an immune response by comparing the immune response to glycosylated and non-glycosylated counterparts. Likewise, sialic acids may constitute an antigenic portion variable among vaccines (Suzuki, 1993, Variation of influenza viruses and their recognition of the receptor sialo-sugar chains, *Yakugaku Zasshi,* 113: 556-78) and may be used as a diagnostic signature sequence.

5.5. Antibody-Based Assays.

Antibody assays are well known to those skilled in the arts and include enzyme-linked immunosorbent assays (ELISAs), immunoblots, protein arrays and many others (Ed Harlow and David Lane, Antibodies, A Laboratory Manual. Cold Spring Harbor Press, 1988, 731 pp). Antibody based assays allow the determination of the presence of antibodies (Cheng et al., 2008, Serologic and genetic characterization analysis of a highly pathogenic influenza virus (H5N1) isolated from an infected man in Shenzhen, J. Med. Virol. 80: 1058-1064; Katz et al., 1999, Antibody response in individuals infected with avian influenza A (H5N1) virus and detection of anti-H5 antibody among household and social contacts. J. Infect. Dis. 180: 1763-1770; Rowe et al., 1999, detection of antibody to avian influenza A (H5N1) virus in human serum using a combination of serologic assays, J. Clin. Microbiol. 37: 937-943). Antibody tests test for the presence of antibodies to a particular antigen, or portion of an antigen or specific epitope. Multiple formats exist, and either an antigen, an antibody, or capture antibody or capture ligand may first be adhered to a substrate, exposing it in a manner that allows a secondary exposure which may contain either the antibodies, antigen, or complex thereof, together with the necessary reporter and or detector, respectively, to bind to the antigen (Ed Harlow and David Lane, Antibodies, A Laboratory Manual. Cold Spring Harbor Press, 1988, 731 pp). By specifically detecting the presence of antibodies and their relative amount, knowledge of immunization to a particular parasite or infectious disease such as an influenza virus, either through immunization of one or more vaccines and vaccine antigens, or through natural exposure, can be ascertained. Various bodily fluids may contain antibodies to influenza, including blood (whole, serum or plasma), saliva, urine or (Ed Harlow and David Lane, Antibodies, A Laboratory Manual. Cold Spring Harbor Press, 1988, 731 pp; Urnovitz et al., 1999, Urine Antibody Tests: New Insights into the Dynamics of HIV-1 Infection Clinical Chemistry 45: 1602-1613; Vazquez et al., 2007, Kinetics of antibodies in sera, saliva, and urine samples from adult patients with primary or secondary dengue 3 virus infections, International Journal of Infectious Diseases 11: 256-262), or other mucus membranes such as the nasopharynx, bronchia or lungs.

In testing for antibody responses, tests for IgM are particularly useful for early testing because they constitute an early antibody response to infectious diseases, although IgG generally have a greater data base of well-described epitopes and persist longer. Immunoglobulin capture such as the "IgM capture" assays have been used for infectious disease exposure (Shaikn et al., 2007, Development of a novel, rapid, and sensitive immunochromatographic strip assay specific for west nile virus (WNV) IgM and testing of its diagnostic accuracy in patients suspected of WNV infection, Clin. Chem. 53: 2031-2034; Song, WO/2008/020293, West Nile virus envelope (e) protein antigen and immunoassay). However, these tests do not distinguish among multiple antigens with varying epitopes originating from one or more vaccines, nor among posttranslational modifications of the vaccine antigens.

6. FIGURE LEGENDS

FIGS. 2A and 2B shows a determination of an epitope region of a sequence based on known epitopic regions. FIG. 2A shows a comparison of GenBank Accession number AF389118; top sequence) with the Genbank Accession number GQ280797 (bottom sequence) using DNA Strider (Douglas, 1995, DNA Strider. An inexpensive sequence analysis package for the Macintosh, *Mol Biotechnol* 3:37-45; middle sequence shows completely homologous regions) for which the hemagglutinin has with a known epitope map (Xu et al., 2010, FIG. 1). FIG. 2B shows an enlargement of the Sa epitope region from Xu et al., 2010, with a double underline for the Sa region, and a box drawn around the corresponding region in GenBank Accession number AF389118, identifying the sequence EKEGSYPKLKNS [SEQ ID NO: 001]. The sequence can be paired with variants or escape mutants to distinguish the immune response between two vaccines.

FIGS. 3A, 3B and 3C show a modification of an epitope for use in a strip assay determining the response to one or more epitopes. FIG. 3B shows the wild type Sa epitope from Hensley et al., 2009 and corresponding amino acids for the generalized structure above, the FLAG epitope, a thrombin cleavage site (for removal of the purification peptide) and a hexahistidine peptide to facilitate purification, with spacer peptides GGG, shown in smaller type in between.

7. DETAILED DESCRIPTION OF THE PREFERRED EMBODIMENTS

In order to more fully illustrate the invention, the following examples are provided.

7.1. Example 1

An Immunochromatographic Strip Assay for IgM Capable for Determination of Successful Vaccination Patients will demonstrate an early antibody response of the IgM type during the first 4 days post vaccine immunization or illness, and nearly all patients will have detectable IgM antibodies by 7 to 8 days thereafter. Influenza-specific serum IgG is detectable by 3 weeks postinfection/inoculation. The virus itself is usually no longer detectable by the time influenza-specific serum IgM appears, although both IgM and IgG may persist for more than a year.

Both the ELISA and the strip format assay can use the same principle and the same antigens. A solid-phase immunochromatographic strip technology to qualitatively detect the presence of antibodies in human serum or plasma has been devised (Shaikh et al., Development of a novel, rapid, and sensitive immunochromatographic strip assay specific for West Nile Virus (WNV) IgM and testing of its diagnostic accuracy in patients suspected of WNV infection, Clin. Chem. 53: 2031-2034) and has been compared with ELISA assays (Tardei et al., 2000, Evaluation of immunoglobin M (IgM) and IgG enzyme immunoassays in serologic diagnosis of West Nile virus infection. J Clin Microbiol 38:2232-2239; Martin et al., 2000, Standardization of immunoglobin M capture enzyme-linked immunosorbent assays for routine diagnosis of arboviral infections. J Clin Microbiol 38:1823-1836; Malan et al., 2004, Evaluation of commercial West Nile virus immunoglobulin G (IgG) and IgM enzyme immunoassays show the value of continuous validation. J Clin Microbiol 42:727-733).

The test herein uses one or more specific influenza antigens such as the hemaggutinin, produced in one or more expression systems, such as a bacterium (e.g., *Escherichia coli*), producing non-glycosylated antigens, or using an insect cell/baculovirus system (Wei et al., 2008, Comparative Efficacy of Neutralizing Antibodies Elicited by Recombinant Hemagglutinin Proteins from Avian H5N1 Influenza Virus, J. Virol., 82: 6200-6208), with or without hexahistidine tag, producing glycosylated antigens (Merten et al., (eds) 2001, Recombinant protein production with prokaryotic and eukaryotic cells; A comparative view on host physiology, Kluwer Academic Publishers; Villayerde and Mattanovich, 2007, Recombinant protein production in the new millennium, Microb. Cell Fact. 6: 33 and references therein). Goat-anti-human IgM is biotinylated (biot-IgM) and a mouse monoclonal IgG anti-antigen antibody is conjugated onto colloidal gold particles (detector component). All 3 reagents are then dispensed onto the polyester pad and lyophilized. Streptavidin is immobilized onto a nitrocellulose (Sartorius) membrane strip at the test-band site. Rabbit antimouse IgG-Fc is immobilized at the control-band site. When the specimen is dispensed into the sample well, it passes through the membrane, which contains antigen, detector, and biot-IgM antibodies. The influenza IgM in the patient sample then forms a tertiary detector/antigen/IgM complex. The formed complex then migrates through the reaction strip and is captured at the test area. Excess, unreacted detector flows through the strip and is captured in the control area. The reactant concentrations are adjusted and optimized by analysis of calibrators, made from pooled influenza-positive sera, so that the test should produce a positive signal at influenza IgM Index value 1.1 of a commercially available IgM Capture ELISA device (Gentaur, Influenza Elisa Kit; comparator device) and negative results below that number.

Figure 1A:
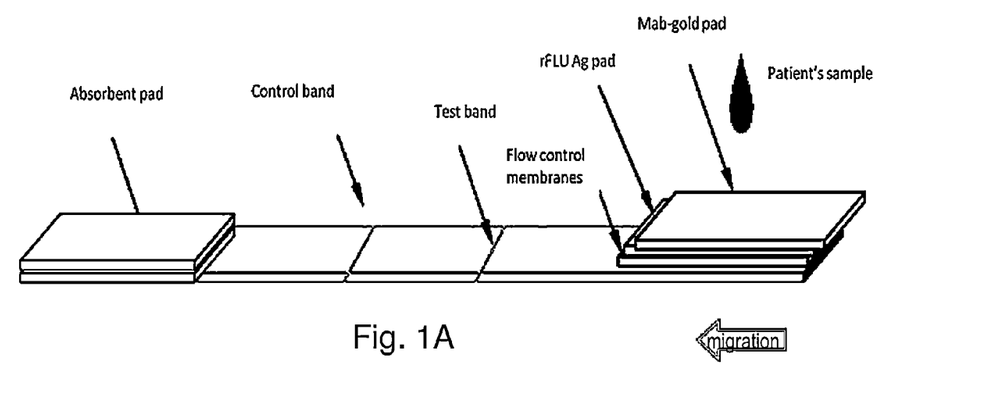
FIG. 1A (top) shows an arrangement of different components in a strip test design and examples of positive (both bands present), negative (test band absent), and invalid (no control band) test results.
Figure 1B:
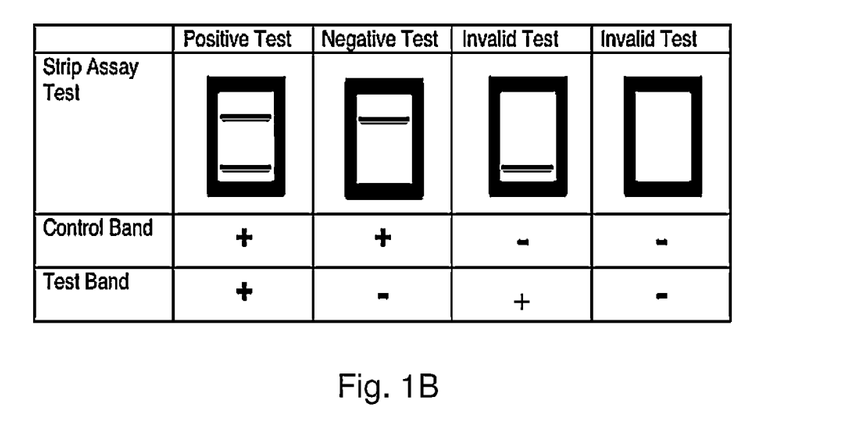
FIG. 1B (Bottom) shows tabular results of the test strip. The positive test results are suggestive of influenza immunity as the IgM levels are at or above the established cut-off level. Invalid results indicate that the test must be repeated. rFLU, recombinant influenza antigen; Mab, monoclonal antibody.

Examples of positive, negative, and invalid test results are shown in FIG. 1B. Visible pinkish-purple horizontal bands appear in the test area if the concentration of the influenza IgM antibodies in the human serum sample is above the cutoff concentration in relation to the comparator device. A pinkish-purple band in the control area indicates that the test is working properly, and such a band must always appear, irrespective of the influenza IgM concentration, for the test to be considered valid.

7.2. Example 2

Selection of One or More Antigenic Epitope Peptides for Influenza H1N1 Hemagglutinin Vaccination Tests Antigens used for determining successful immunization are the antigens of a vaccine for which the test is specifically designed to assess. Thus, if a vaccine used a particular hemagglutinin, such as that of Genbank Accession number GQ280797, then the same hemaggutinin can be used to test for vaccination. If more than one vaccine is to be tested for within a single patient, specific areas of the antigen must be selected. The comparison of antigens that are present in different vaccines is based upon knowledge of the current vaccine compositions for which testing is desired. Antigen epitope peptides are selected based upon known antigenic sights, such as Sa, Sb, Ca, and Cb, based on epitope mapping. Prior epitope maps may be used, such as that described by Xu et al., 2010 (Structural basis of preexisting immunity to the 2009 H1N1 pandemic influenza, Science 328: 357-360) in order to determine the epitopic region of a new antigen. Hensley et al., 2009 have described escape mutants of an H1N1 influenza. The complete protein sequence of that hemagglutinin (GenBank Accession number AF389118) is compared with the Genbank Accession number GQ280797 for which the hemagglutinin has with a known epitope map (Xu et al., 2010, FIG. 1). The comparison of these two proteins, using the algorithm for DNA Strider (Douglas, 1995, DNA Strider. An inexpensive sequence analysis package for the Macintosh, *Mol Biotechnol* 3:37-45), is shown in FIGS. 2A and 2B. The homologous region is determined by amino acid homology, and the epitope of the sequence in question, EKEGSYPKLKNS [SEQ ID NO: 001], ascertained. A comparative test for vaccination by the escape mutant, which could occur with a vaccine made after the escape variant was isolated, can be performed using the escape mutant epitope, EKKGSYPKLKNS [SEQ ID NO: 002] described by Hensley et al., 2009 (amino acid variant shown in bold).

7.3. Example 3

Construction of Peptides for IgG Immunochromatographic Strip Assays

Figure 3A:
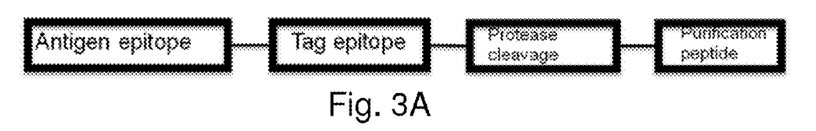
FIG. 3A shows an example of a generalized structure of a peptide which may be recombinantly produced, consisting of the antigenic epitope, optionally a spacer peptide, a tag epitope, optionally a spacer peptide, a protease cleavage site (downward arrow shows cleavage location), optionally a spacer peptide, and a peptide to facilitate purification.
Figure 3B:
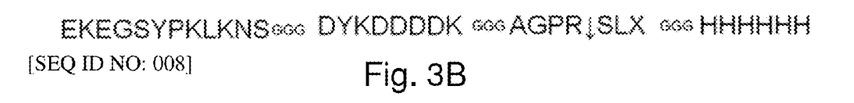
Figure 3C:
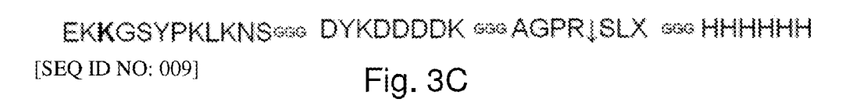
FIG. 3C shows the same structure in B with an escape variant of the Sa epitope (E to K mutation in bold).

In order to modify the immunochomatographic strip assay to accommodate IgG, the epitope peptides must be tagged with an epitope tag in order to be recognized by a gold-conjugated detector antibody that is not recognized by an anti-human IgG biotinylated capture antibody. The test herein uses one or more specific fragments of recombinant influenza antigens (signature epitopes, such as those from Table 1, also described in the Example above) that are expressed as a fusion protein with specific antibody tags (e.g., epitope tags such as FLAG (DYKDDDDK) [SEQ ID NO: 003] or myc (EQKLISEEDL) [SEQ ID NO: 004] Jarvik and Telmer, 1998, Epitope tagging, Annual Review of Genetics, 32: 601-618), in one or more expression systems, such as a bacterium (Merten et al., (eds) 2001, Recombinant protein production with prokaryotic and eukaryotic cells; A comparative view on host physiology, Kluwer Academic Publishers; Villayerde and Mattanovich, 2007, Recombinant protein production in the new millennium, Microb. Cell Fact. 6: 33 and references therein). An diagram of a suitable peptide construct and representative peptides for Sa epitopes and a specific corresponding escape mutant of the same epitope is shown in FIGS. 3A, 3B and 3C.

7.4. Example 4

A Multivalent Immunochromatographic Strip Assay for IgG Capable of Distinguishing Patients Immunized with Different Hemagglutinins Variants The test herein uses one or more specific fragments of recombinant influenza antigens (signature epitopes, such as those from Table 1) that are expressed as a fusion protein with specific antibody tags (epitope tags such as FLAG (DYKDDDDK) [SEQ ID NO: 003] or myc (EQKLISEEDL) [SEQ ID NO: 004] Jarvik and Telmer, 1998, Epitope tagging, Annual Review of Genetics, 32: 601-618), in one or more expression systems, such as a bacterium (*Escherichia coli*; with or without hexahistidine (HHHHHH)-tag) [SEQ ID NO: 005], producing non-glycosylated antigens, or using an insect cell/baculovirus system (Wei et al., 2008, Comparative Efficacy of Neutralizing Antibodies Elicited by Recombinant Hemagglutinin Proteins from Avian H5N1 Influenza Virus, J. Virol., 82: 6200-6208), with or without hexahistidine tag, producing glycosylated antigens (Merten et al., (eds) 2001, Recombinant protein production with prokaryotic and eukaryotic cells; A comparative view on host physiology, Kluwer Academic Publishers; Villayerde and Mattanovich, 2007, Recombinant protein production in the new millennium, Microb. Cell Fact. 6: 33 and references therein), as described above and depicted in FIGS. 3A, 3B and 3C. Separate parallel strips may be constructed with each of the particular antigens. Goat-antihuman IgG is biotinylated (biot-IgG) and a non-crossreactive mouse monoclonal IgG anti-TAG antibody (i.e., not recognized by the goat anti-human IgG) is conjugated onto colloidal gold particles (detector component). All 3 reagents are then dispensed onto the polyester pad and lyophilized. Streptavidin is immobilized onto a nitrocellulose (Sartorius) membrane strip at the test-band site. Rabbit antimouse IgG-Fc is immobilized at the control-band site. When the specimen is dispensed into the sample well, it passes through the membrane, which contains antigen, detector, and biot-IgG antibodies. The influenza IgG in the patient sample then forms a tertiary detector/antigen/IgG complex. The formed complex then migrates through the reaction strip and is captured at the test area. Excess, unreacted detector flows through the strip and is captured in the control area. The reactant concentrations are adjusted and optimized by analysis of calibrators, made from pooled influenza-positive sera, so that the test should produce a positive signal at influenza IgG Index value 1.1 of a commercially available IgM Capture ELISA device (Gentaur, Influenza Elisa Kit; comparator device) and negative results below that number.

Figure 4:
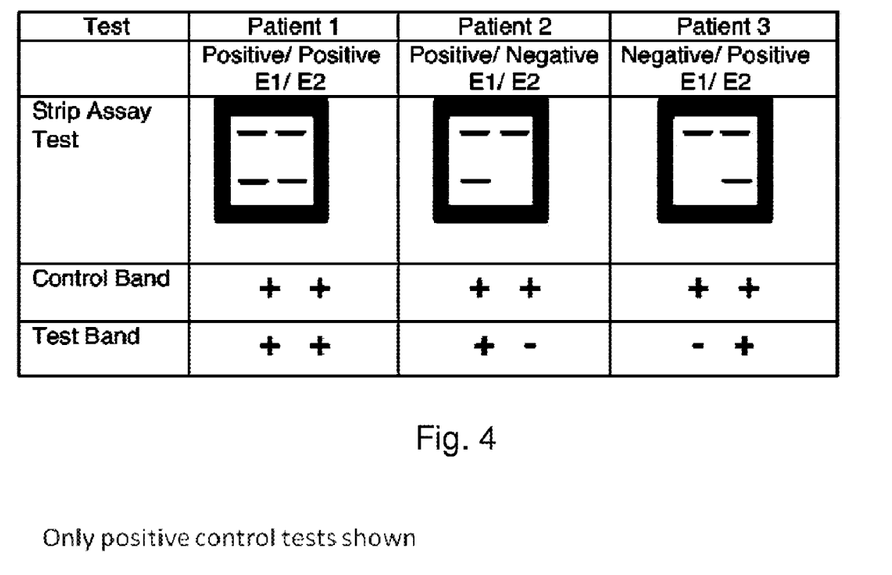
FIG. 4 shows the tabular results of a test strip with two representative set of finger print peptide sequences for two epitopes (E1 and E2) of H1 hemagglutinins, where the first epitope is described in FIG. 3B and the second epitope is described in FIG. 3C. The results are shown for 3 different patients. Patient 1 is positive for both hemagglutinin epitopes and therefore has been exposed to both types. Patient 2 is positive only for E1. Patient 3 is positive for only E2.

Examples of multivalent positive and negative results are shown in FIG. 4. Visible pinkish-purple horizontal bands appear in the test area if the concentration of the influenza IgG antibodies in the human serum sample is above the cutoff concentration in relation to the comparator device. A pinkish-purple band in the control area indicates that the test is working properly, and such a band must always appear, irrespective of the influenza IgG concentration, for the test to be considered valid. In FIG. 4 results of a test strip with two representative set of finger print peptide sequences for two epitopes (E1 and E2) of H1 hemagglutinins, where the first epitope is described in FIG. 3B and the second epitope is described in FIG. 3C. The results are shown for 3 different patients. Patient 1 is positive for both hemagglutinin epitopes and therefore has been exposed to both types. Patient 2 is positive only for E1. Patient 3 is positive for only E2. If it is known that all three patients have been given two types of vaccines, one corresponding to E1 and one corresponding to E2, then the additional interpretation is that in patient 1, both vaccines were successful, and that in patients two and three, only one of the two vaccines were successful. Knowledge of this success can guide patients, especially the elderly, to seek additional vaccination if necessary, and can guide healthcare workers and those seeking to understand the efficacy of vaccines which vaccines are successful and which are not, even when the patients have received more than one vaccine.

The various aspects of the disclosure may be combined and subcombined to represent all consistent combinations and subcombinations without departing from the scope of the invention. The invention is limited by neither the specific embodiments of the specification, nor the particular scope of the claims, but rather is to be treated as encompassing the full scope of each aspect disclosed, and the various combinations and permutations, which do not depart from the enabled disclosure herein.

What is claimed is:

1. A test system for presence of host antigen-specific antibodies, comprising:
   a reactant layer, into which are absorbed the antigen, an anti-host IgM bound to a ligand, and a detector comprising a non-host anti-antigen IgG conjugated to colloidal particles;
   a test strip, in fluid communication with the reactant layer at a portion thereof, to which a ligand binding agent is immobilized at a test area and an anti-non-host IgG is immobilized at a control area, the test area being spaced more proximate to the reactant layer than the control area; and
   a sample well,
   wherein host antigen-specific antibodies in a specimen of serum from the host placed in the sample well selectively form a quaternary complex with a ternary complex formed from the detector, the antigen and the anti-host IgM bound to a ligand, which migrates through the test strip and is captured by the immobilized ligand binding agent at the test area, and the ternary complex unbound to host antigen-specific antibodies flow past the test area and are captured by the immobilized anti-non-host IgG at the control area, to thereby show presence of the host antigen-specific antibodies by an indication at the test area and validity by an indication at the control area.

2. The test system according to claim 1, wherein the ligand is biotin and the ligand binding agent is strepavidin.

3. The test system according to claim 1, wherein the colloidal particles are gold particles.

4. The test system according to claim 1, wherein the concentrations of antigen, anti-host IgM bound to the ligand, the detector, immobilized ligand binding agent and the immobilized anti-non-host IgG are provided, based on calibration with pooled sera from successfully immunized hosts, to produce a positive indication at an IgM Index value of at least 1.1 of an IgM Capture ELISA device and a negative indication results below an IgM Index value of 1.1 of the IgM Capture ELISA device.

5. The test system according to claim 1, wherein the antigen is an influenza hemagglutinin.

6. The test system according to claim 5, wherein the antigen is an influenza hemagglutinin produced by a genetically engineered bacterium.

7. The test system according to claim 1, wherein the antigen is a glycosylated antigen produced in an insect cell/baculovirus system.

8. The test system according to claim 1, wherein the anti-host IgM comprises biotinylated goat-antihuman IgM.

9. The test system according to claim 1, wherein the non-host anti-antigen IgG comprises mouse monoclonal anti-antigen IgG.

10. The test system according to claim 9 wherein the anti-non-host IgG immobilized at the control area comprises rabbit antimouse IgG-Fc.

11. The test system according to claim 10, wherein the mouse monoclonal anti-antigen IgG is conjugated onto colloidal gold particles.

12. The test system according to claim 1, wherein the antigen, the anti-host IgM bound to the ligand, and the detector are dispensed as at least one solution on the reactant layer and subsequently lyophilized.

13. The test system according to claim 1, wherein the reactant layer comprises a polyester pad.

14. The test system according to claim 1, wherein the test strip comprises a nitrocellulose membrane.

15. The test system according to claim 1, wherein the test strip comprises an elongated strip, on which the reactant layer is situated on one side, and the test area and control area are sequentially disposed distant from the test strip, and the sample well is on top of the reactant layer, and between the reactant layer and the test strip is disposed at least one flow control layer, further comprising an absorbent pad in fluid communication with the test strip disposed on an opposite side of the control area from the reactant layer, wherein the absorbent pad induces a bulk fluid flow from the reactant layer to the absorbent pad.

16. The test system according to claim 1, wherein:
   the ligand is biotin and the ligand binding agent is strepavidin;
   the colloidal particles are colloidal gold particles;
   the anti-host IgM bound to a ligand comprises biotinylated goat-antihuman IgM;
   the non-host anti-antigen IgG comprises mouse monoclonal anti-antigen IgG; and
   the anti-non-host IgG immobilized at the control area comprises rabbit antimouse IgG-Fc,
   further comprising an absorbent pad in fluid communication with the test strip disposed on an opposite side of the control area from the reactant layer, wherein the absorbent pad induces a bulk fluid flow from the reactant layer to the absorbent pad,
   wherein the antigen, the anti-host IgM bound to a ligand, and the detector are dispensed as at least one solution on the reactant layer and subsequently lyophilized, the reactant layer comprises a polyester pad, the test strip comprises a nitrocellulose membrane, and the test strip comprises an elongated strip, on which the reactant layer is situated on one side, the test area and control area are sequentially disposed distant from the test strip, and the sample well is on top of the reactant layer, and between the reactant layer and the test strip is disposed at least one flow control layer, and
   wherein the concentrations of antigen, anti-host IgM bound to the ligand, the detector, immobilized ligand binding agent and immobilized anti-non-host IgG are provided, based on calibration with pooled sera from successfully immunized hosts, to produce a positive indication at an IgM Index value of at least 1.1 of an IgM Capture ELISA device and a negative indication results below an IgM Index value of 1.1 of the IgM Capture ELISA device.

17. The test system according to claim 1, wherein the epitope peptide is an epitope hemagglutinin peptide modified to be covalently bound to a non-hemagglutinin non-hemaggutinin epitope peptide.

18. A system for testing for presence of host antigen-specific antibodies to an antigen from a host, comprising:
- a reactant layer, into which are absorbed the antigen, an anti-host IgM bound to a ligand, and a detector comprising a non-host anti-antigen IgG conjugated to colloidal particles, to form a ternary detector/antigen/anti-host IgM complex;

a test strip, in fluid communication with the reactant layer at a portion thereof, to which a ligand binding agent is immobilized at a test area and an anti-non-host IgG is immobilized at a control area, the test area being spaced more proximate to the reactant layer than the control area; and a sample well, the system being configured such that:

a serum specimen from a host may be placed in the sample well;

host antigen-specific antibodies in the serum specimen selectively form a quaternary host antigen-specific antibodies/detector/antigen/anti-host IgM complex with the ternary detector/antigen/anti-host IgM complex;

quaternary host antigen-specific antibodies/detector/antigen/anti-host IgM complex which migrates through the test strip are captured at the test area by the immobilized ligand binding agent; and the ternary detector/antigen/anti-host IgM complex unbound to antigen-specific host antibodies which migrates through the test strip, are captured at the control area past the test area, by the immobilized anti-non-host IgG, to thereby indicate a presence of the host antigen-specific antibodies by an indication at the test area and validity of the test by an indication at the control area.

19. The system according to claim 18, wherein:

the ligand is biotin and the ligand binding agent is strepavidin;

the colloidal particles are colloidal gold particles;

the anti-host IgM bound to a ligand comprises biotinylated goat-antihuman IgM;

the non-host anti-antigen IgG comprises mouse monoclonal anti-antigen IgG; and the anti-non-host IgG immobilized at the control area comprises rabbit antimouse IgG-Fc, an absorbent pad in fluid communication with the test strip is disposed on an opposite side of the control area from the reactant layer, wherein the absorbent pad is configured to induce a bulk fluid flow from the reactant layer to the absorbent pad; and the antigen, the anti-host IgM bound to the ligand, and the detector are provided as at least one solution on the reactant layer and subsequently lyophilized, the reactant layer comprising a polyester pad, the test strip comprises a nitrocellulose membrane, and the test strip comprising an elongated strip, on which the reactant layer is situated on one side, the test area and control area being sequentially disposed distant from the test strip, and the sample well being on top of the reactant layer, and at least one flow control layer is disposed between the reactant layer and the test strip.

20. A test system for determining presence of host antigen-specific antibodies, comprising:

a reactant layer, into which are absorbed the antigen, an anti-host IgM bound to a ligand, and a detector comprising a non-host anti-antigen IgG conjugated to colloidal particles forming a ternary complex;

a test strip in fluid communication with the reactant layer at a portion thereof, having a ligand binding agent immobilized at a test area of the test strip and an anti-non-host IgG immobilized at the control area a test strip, the test area being spaced more proximate to the reactant layer than the control area; and a sample well, wherein the host antigen-specific antibodies in a specimen of serum from the host placed in the sample well selectively form a quaternary complex with the ternary complex which migrates through the test strip and is captured by the immobilized ligand binding agent at the test area, and the ternary complex unbound to host antigen-specific antibodies flow past the test area and are captured by the immobilized anti-non-host IgG at the control area, to thereby show presence of the host antigen-specific antibodies by an indication at the test area, and show validity by an indication at the control area.

* * * * *

SEQUENCE LISTING

<160> NUMBER OF SEQ ID NOS: 8

<210> SEQ ID NO 1
<211> LENGTH: 12
<212> TYPE: PRT
<213> ORGANISM: Influenza A virus

<400> SEQUENCE: 1

Glu Lys Glu Gly Ser Tyr Pro Lys Leu Lys Asn Ser
1               5                   10

<210> SEQ ID NO 2
<211> LENGTH: 12
<212> TYPE: PRT
<213> ORGANISM: Influenza A virus

<400> SEQUENCE: 2

Glu Lys Lys Gly Ser Tyr Pro Lys Leu Lys Asn Ser
1               5                   10

<210> SEQ ID NO 3
<211> LENGTH: 8
<212> TYPE: PRT
<213> ORGANISM: Artificial Sequence
<220> FEATURE:
<223> OTHER INFORMATION: FLAG epitope specific antibody tag

<400> SEQUENCE: 3

Asp Tyr Lys Asp Asp Asp Asp Lys
1               5

<210> SEQ ID NO 4
<211> LENGTH: 10
<212> TYPE: PRT
<213> ORGANISM: Artificial Sequence
<220> FEATURE:
<223> OTHER INFORMATION: myc epitope specific antibody tag

<400> SEQUENCE: 4

Glu Gln Lys Leu Ile Ser Glu Glu Asp Leu
1               5                   10

<210> SEQ ID NO 5
<211> LENGTH: 6
<212> TYPE: PRT
<213> ORGANISM: Artificial Sequence
<220> FEATURE:
<223> OTHER INFORMATION: hexahistidine coding and affinity purification
      tag

<400> SEQUENCE: 5

His His His His His His
1               5

<210> SEQ ID NO 6
<211> LENGTH: 565
<212> TYPE: PRT
<213> ORGANISM: Influenza A virus

<400> SEQUENCE: 6

Met Lys Ala Asn Leu Leu Val Leu Leu Ser Ala Leu Ala Ala Ala Asp
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn

```
                35                  40                  45
Leu Leu Glu Asp Ser His Asn Gly Lys Leu Cys Arg Leu Lys Gly Ile
                50                  55                  60
Ala Pro Leu Gln Leu Gly Lys Cys Asn Ile Ala Gly Trp Leu Leu Gly
 65                  70                  75                  80
Asn Pro Glu Cys Asp Pro Leu Leu Pro Val Arg Ser Trp Ser Tyr Ile
                 85                  90                  95
Val Glu Thr Pro Asn Ser Glu Asn Gly Ile Cys Tyr Pro Gly Asp Phe
                100                 105                 110
Ile Asp Tyr Glu Glu Leu Arg Glu Gln Leu Ser Ser Val Ser Ser Phe
                115                 120                 125
Glu Arg Phe Glu Ile Phe Pro Lys Glu Ser Ser Trp Pro Asn His Asn
                130                 135                 140
Thr Asn Gly Val Thr Ala Ala Cys Ser His Glu Gly Lys Ser Ser Phe
145                 150                 155                 160
Tyr Arg Asn Leu Leu Trp Leu Thr Glu Lys Glu Gly Ser Tyr Pro Lys
                165                 170                 175
Leu Lys Asn Ser Tyr Val Asn Lys Lys Gly Lys Glu Val Leu Val Leu
                180                 185                 190
Trp Gly Ile His His Pro Pro Asn Ser Lys Glu Gln Gln Asn Ile Tyr
                195                 200                 205
Gln Asn Glu Asn Ala Tyr Val Ser Val Val Thr Ser Asn Tyr Asn Arg
210                 215                 220
Arg Phe Thr Pro Glu Ile Ala Glu Arg Pro Lys Val Arg Asp Gln Ala
225                 230                 235                 240
Gly Arg Met Asn Tyr Tyr Trp Thr Leu Leu Lys Pro Gly Asp Thr Ile
                245                 250                 255
Ile Phe Glu Ala Asn Gly Asn Leu Ile Ala Pro Met Tyr Ala Phe Ala
                260                 265                 270
Leu Ser Arg Gly Phe Gly Ser Gly Ile Ile Thr Ser Asn Ala Ser Met
                275                 280                 285
His Glu Cys Asn Thr Lys Cys Gln Thr Pro Leu Gly Ala Ile Asn Ser
                290                 295                 300
Ser Leu Pro Tyr Gln Asn Ile His Pro Val Thr Ile Gly Glu Cys Pro
305                 310                 315                 320
Lys Tyr Val Arg Ser Ala Lys Leu Arg Met Val Thr Gly Leu Arg Asn
                325                 330                 335
Thr Pro Ser Ile Gln Ser Arg Gly Leu Phe Gly Ala Ile Ala Gly Phe
                340                 345                 350
Ile Glu Gly Gly Trp Thr Gly Met Ile Asp Gly Trp Tyr Gly Tyr His
                355                 360                 365
His Gln Asn Glu Gln Gly Ser Gly Tyr Ala Ala Asp Gln Lys Ser Thr
                370                 375                 380
Gln Asn Ala Ile Asn Gly Ile Thr Asn Lys Val Asn Thr Val Ile Glu
385                 390                 395                 400
Lys Met Asn Ile Gln Phe Thr Ala Val Gly Lys Glu Phe Asn Lys Leu
                405                 410                 415
Glu Lys Arg Met Glu Asn Leu Asn Lys Lys Val Asp Asp Gly Phe Leu
                420                 425                 430
Asp Ile Trp Thr Tyr Asn Ala Glu Leu Leu Val Leu Leu Glu Asn Glu
                435                 440                 445
Arg Thr Leu Asp Phe His Asp Ser Asn Val Lys Asn Leu Tyr Glu Lys
                450                 455                 460
```

```
Val Lys Ser Gln Leu Lys Asn Asn Ala Lys Glu Ile Gly Asn Gly Cys
465                 470                 475                 480

Phe Glu Phe Tyr His Lys Cys Asp Asn Glu Cys Met Glu Ser Val Arg
                485                 490                 495

Asn Gly Thr Tyr Asp Tyr Pro Lys Tyr Ser Glu Glu Ser Lys Leu Asn
            500                 505                 510

Arg Glu Lys Val Asp Gly Val Lys Leu Glu Ser Met Gly Ile Tyr Gln
            515                 520                 525

Ile Leu Ala Ile Tyr Ser Thr Val Ala Ser Ser Leu Val Leu Leu Val
            530                 535                 540

Ser Leu Gly Ala Ile Ser Phe Trp Met Cys Ser Asn Gly Ser Leu Gln
545                 550                 555                 560

Cys Arg Ile Cys Ile
            565

<210> SEQ ID NO 7
<211> LENGTH: 566
<212> TYPE: PRT
<213> ORGANISM: Influenza A virus

<400> SEQUENCE: 7

Met Lys Ala Ile Leu Val Val Leu Leu Tyr Thr Phe Ala Thr Ala Asn
1               5                   10                  15

Ala Asp Thr Leu Cys Ile Gly Tyr His Ala Asn Asn Ser Thr Asp Thr
                20                  25                  30

Val Asp Thr Val Leu Glu Lys Asn Val Thr Val Thr His Ser Val Asn
            35                  40                  45

Leu Leu Glu Asp Lys His Asn Gly Lys Leu Cys Lys Leu Arg Gly Val
50                  55                  60

Ala Pro Leu His Leu Gly Lys Cys Asn Ile Ala Gly Trp Ile Leu Gly
65                  70                  75                  80

Asn Pro Glu Cys Glu Ser Leu Ser Thr Ala Ser Ser Trp Ser Tyr Ile
                85                  90                  95

Val Glu Thr Pro Ser Ser Asp Asn Gly Thr Cys Tyr Pro Gly Asp Phe
            100                 105                 110

Ile Asp Tyr Glu Glu Leu Arg Glu Gln Leu Ser Ser Val Ser Ser Phe
            115                 120                 125

Glu Arg Phe Glu Ile Phe Pro Lys Thr Ser Ser Trp Pro Asn His Asp
130                 135                 140

Ser Asn Lys Gly Val Thr Ala Ala Cys Pro His Ala Gly Ala Lys Ser
145                 150                 155                 160

Phe Tyr Lys Asn Leu Ile Trp Leu Val Lys Lys Gly Asn Ser Tyr Pro
                165                 170                 175

Lys Leu Ser Lys Ser Tyr Ile Asn Asp Lys Gly Lys Glu Val Leu Val
            180                 185                 190

Leu Trp Gly Ile His His Pro Ser Thr Ser Ala Asp Gln Gln Ser Ile
            195                 200                 205

Tyr Gln Asn Ala Asp Thr Tyr Val Phe Val Gly Ser Ser Arg Tyr Ser
210                 215                 220

Lys Lys Phe Lys Pro Glu Ile Ala Ile Arg Pro Lys Val Arg Asp Gln
225                 230                 235                 240

Glu Gly Arg Met Asn Tyr Tyr Trp Thr Leu Val Glu Pro Gly Asp Lys
                245                 250                 255

Ile Thr Phe Glu Ala Thr Gly Asn Leu Val Val Pro Arg Tyr Ala Phe
```

```
                260                 265                 270
Ala Met Glu Arg Asn Ala Gly Ser Gly Ile Ile Ile Ser Asp Thr Pro
            275                 280                 285

Val His Asp Cys Asn Thr Thr Cys Gln Thr Pro Lys Gly Ala Ile Asn
    290                 295                 300

Thr Ser Leu Pro Phe Gln Asn Ile His Pro Ile Thr Ile Gly Lys Cys
305                 310                 315                 320

Pro Lys Tyr Val Lys Ser Thr Lys Leu Arg Leu Ala Thr Gly Leu Arg
                325                 330                 335

Asn Ile Pro Ser Ile Gln Ser Arg Gly Leu Phe Gly Ala Ile Ala Gly
            340                 345                 350

Phe Ile Glu Gly Gly Trp Thr Gly Met Val Asp Gly Trp Tyr Gly Tyr
        355                 360                 365

His His Gln Asn Glu Gln Gly Ser Gly Tyr Ala Ala Asp Leu Lys Ser
    370                 375                 380

Thr Gln Asn Ala Ile Asp Glu Ile Thr Asn Lys Val Asn Ser Val Ile
385                 390                 395                 400

Glu Lys Met Asn Thr Gln Phe Thr Ala Val Gly Lys Glu Phe Asn His
                405                 410                 415

Leu Glu Lys Arg Ile Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
        435                 440                 445

Glu Arg Thr Leu Asp Tyr His Asp Ser Asn Val Lys Asn Leu Tyr Glu
    450                 455                 460

Lys Val Arg Ser Gln Leu Lys Asn Asn Ala Lys Glu Ile Gly Asn Gly
465                 470                 475                 480

Cys Phe Glu Phe Tyr His Lys Cys Asp Asn Thr Cys Met Glu Ser Val
                485                 490                 495

Lys Asn Gly Thr Tyr Asp Tyr Pro Lys Tyr Ser Glu Glu Ala Lys Leu
            500                 505                 510

Asn Arg Glu Glu Ile Asp Gly Val Lys Leu Glu Ser Thr Arg Ile Tyr
        515                 520                 525

Gln Ile Leu Ala Ile Tyr Ser Thr Val Ala Ser Ser Leu Val Leu Val
    530                 535                 540

Val Ser Leu Gly Ala Ile Ser Phe Trp Met Cys Ser Asn Gly Ser Leu
545                 550                 555                 560

Gln Cys Arg Ile Cys Ile
                565

<210> SEQ ID NO 8
<211> LENGTH: 42
<212> TYPE: PRT
<213> ORGANISM: Artificial Sequence
<220> FEATURE:
<223> OTHER INFORMATION: Wild type Sa epitope (Hensley et al. 2009),
      FLAG epitope tag, Thrombin cleavage site (AGPR-SLX),
      Hexahistidine tag
<220> FEATURE:
<221> NAME/KEY: misc_feature
<222> LOCATION: (33)..(33)
<223> OTHER INFORMATION: Xaa can be any naturally occurring amino acid

<400> SEQUENCE: 8

Glu Lys Glu Gly Ser Tyr Pro Lys Leu Lys Asn Ser Gly Gly Gly Asp
1               5                   10                  15
```

```
Tyr Lys Asp Asp Asp Asp Lys Gly Gly Gly Ala Gly Pro Arg Ser Leu
            20                  25                  30

Xaa Gly Gly Gly His His His His His His
        35                  40
```